United States Patent [19]
Galley et al.

[11] Patent Number: 5,609,852
[45] Date of Patent: Mar. 11, 1997

[54] SUNSCREEN WITH COATED MICROFINE PARTICLES

[75] Inventors: Edward Galley; Nicola A. Fardell, both of Nottinghamshire, England

[73] Assignee: The Boots Company PLC, United Kingdom

[21] Appl. No.: 338,470
[22] PCT Filed: May 12, 1993
[86] PCT No.: PCT/EP93/01179
§ 371 Date: Nov. 16, 1994
§ 102(e) Date: Nov. 16, 1994
[87] PCT Pub. No.: WO93/23483
PCT Pub. Date: Nov. 25, 1993

[30] Foreign Application Priority Data

May 16, 1992 [GB] United Kingdom .................. 9210516

[51] Int. Cl.$^6$ ...................................................... A61K 7/42
[52] U.S. Cl. ............................ 424/59; 106/425; 106/428; 423/609; 423/622
[58] Field of Search ............................. 424/59; 423/608, 423/622; 106/419

[56] References Cited

U.S. PATENT DOCUMENTS

| | | | |
|---|---|---|---|
| 4,323,554 | 4/1982 | Bernhard | 424/63 |
| 4,847,071 | 7/1989 | Bissett et al. | 424/59 |
| 5,143,723 | 9/1992 | Calvo et al. | 424/63 |

FOREIGN PATENT DOCUMENTS

| | | |
|---|---|---|
| 0266247 | 5/1988 | European Pat. Off. . |
| 0433086 | 6/1991 | European Pat. Off. . |
| 55-013714 | 1/1980 | Japan . |
| 55-071760 | 5/1980 | Japan . |
| 1157908 | 6/1989 | Japan . |
| 3-041168 | 2/1991 | Japan . |
| 9310190 | 5/1993 | WIPO . |

*Primary Examiner*—Shelley A. Dodson
*Attorney, Agent, or Firm*—Ostrolenk, Faber, Gerb & Soffen, LLP

[57] ABSTRACT

The preparation of metal oxide particles having a dye lake precipitated onto their surface in a dye lake:metal oxide ratio of between 10:90 and 80:20 and the use of such particles in cosmetic and toiletry formulations are described.

7 Claims, No Drawings

SUNSCREEN WITH COATED MICROFINE PARTICLES

The present invention relates to coated particles for use in cosmetic and toiletry formulations.

The present invention provides metal oxide particles having a dye lake precipitated onto their surface in a dye lake:metal oxide ratio of between 10:90 and 80:20.

It has been found that water soluble dyes can be used to colour metal oxide particles by a process known as laking. A dye lake is an insoluble precipitate formed by reaction of a metal ion with a water-soluble dye, which can be precipitated onto the surface of a substrate. In the present invention the said metal oxide particles act as the substrate onto which the dye lake can precipitate.

Dyes which act in this respect include azo dyes, triphenylmethane dyes, anthraquinone dyes, indigoid dyes, quinoline dyes, pyrazole dyes, xanthene dyes, fluoran dyes and azine dyes, examples of which are included in Table 1.

TABLE 1

| Dye | Chemical Type | Colour Index No. |
| --- | --- | --- |
| D & C Red no.6 | Monoazo | 15850 |
| D & C Orange no.4 | Monoazo | 15510 |
| FD & C Red no.4 | Monoazo | 14700 |
| Acid Red 27 | Monoazo | 16185 |
| D & C Red no.33 | Monoazo | 17200 |
| FD & C Red no.40 | Monoazo | 16035 |
| FD & C Yellow no.6 | Monoazo | 15985 |
| Acid Yellow 23 | Monoazo | 19140 |
| D & C Yellow no.10 | Quinoline | 47005 |
| FD & C Yellow no.5 | Pyrazole | 19140 |
| Basic Violet 10 | Xanthene | 45170 |
| D & C Yellow no.8 | Xanthene | 45350 |
| D & C Red no.30 | Indigoid | 73360 |
| FD & C Blue no.1 | Triphenylmethane | 42090 |
| FD & C Green no.3 | Triphenylmethane | 42053 |
| D & C Red no.21 | Fluoran | 45380:2 |
| D & C Red no.27 | Fluoran | 35410:1 |
| D & C Orange no.5 | Fluoran | 45370:1 |
| D & C Orange no.10 | Fluoran | 45425:1 |
| D & C Yellow no.7 | Fluoran | 45350:1 |
| Acid Blue 74 | Indigoid | 73015 |

The metal oxide particles of the present invention preferably comprise titanium dioxide, zinc oxide, or mixtures thereof. The titanium dioxide particles preferably have a primary particle size of less than 100 nm and the zinc oxide particles preferably have a primary particle size of less than 500 nm.

One aspect of the present invention provides titanium dioxide particles having a mean primary particle size of less than 100 nm and having a dye lake precipitated onto their surface in a dye lake:titanium dioxide ratio of between 10:90 and 80:20. Preferably the ratio is between 20:80 and 70:30.

A further aspect of the present invention provides zinc oxide particles having a mean primary particle size of less than 500 nm and having a dye precipitated onto their surface in a dye lake:zinc oxide ratio of between 10:90 and 80:20. Preferably the ratio is between 20:80 and 70:30.

The advantage of precipitating a dye lake onto metal oxide particles is that the resulting coloured particles are transparent or translucent to visible light but offer a high degree of opacity to ultra violet light. This feature is useful in the cosmetic and toiletry industries.

The art of making dye lakes is exemplified in U.S. Pat. No. 833,602 issued in 1906 and UK Patent 1,467,548 filed 16 July 1975 and is discussed in the article "A Review of the Literature on Color Lakes", American Dyestuff Reporter, Vol. 35, No. 23, Nov. 1946.

The metal oxide particles of the present invention may be formed by the precipitation of insoluble salts from a solution of dye added to a slurry of metal oxide particles with stirring. Precipitation may be facilitated by addition of a soluble salt of an alkaline earth metal or a soluble salt of a transition metal to the metal oxide slurry at the start of the process. Preferred facilitators are soluble salts of calcium, barium, strontium, manganese, aluminium, zinc, copper, iron, titanium, gallium and magnesium. The pH conditions may be any commonly used in lake formation, and may be varied by any conventional pH modifier.

The metal oxide particles of the present invention are separated by filtration of the mixture, with subsequent washing, drying and grinding to a size suitable for use in cosmetic and toiletry formulations.

The above procedures are particularly suited to the preparation of titanium dioxide particles, preferably having a mean primary particle size in the range 1 to 100 nm, having a dye lake precipitated onto their surface in a dye lake:titanium dioxide ratio of between 10:90 and 80:20. The titanium dioxide functions as the substrate with an adsorptive surface onto which the dye lake can precipitate.

An analogous procedure can be applied to zinc oxide particles preferably having a mean primary particle size in the range 1 to 500 nm. The present invention therefore provides zinc oxide particles having a mean primary particle size in the range 1 to 500 nm and having a dye lake precipitated onto their surface in a dye lake:zinc oxide ratio of between 10:90 and 80:20. In this case, the zinc oxide functions as the substrate with an adsorptive surface onto which the dye lake can precipitate.

The particles of the present invention may be used to prepare cosmetic and toiletry compositions, for example, sunscreens, face powders, blush powders, eye shadow powders, lipsticks, mascaras, nail polish bases and foundation creams.

The metal oxide particles in the above compositions are preferably:

a) titanium dioxide particles having a mean primary particle size of less than 100 nm, b) zinc oxide particles having a mean primary particle size of less than 500 nm, or c) mixtures thereof in a ratio of between 1:99 and 90:10 of titanium dioxide:zinc oxide, more preferably of between 5:95 and 60:40.

Preferred sunscreen compositions comprise the titanium dioxide particles of the present invention.

The use of titanium dioxide as a sunscreening agent is well known. The term "sunscreen" is used herein to encompass tanning lotions, sunscreens and sunblockers which are intended for use on the body to provide protection against the sun's rays or other UV sources. The amount of titanium dioxide present in a sunscreen composition depends on the use for which the composition is intended. Amounts as low as 1% by weight may be sufficient in the so-called suntanning products which are not intended to prevent the sun's rays reaching the skin whereas the so-called sunblocks which are intended to prevent substantially all of the sun's rays reaching the skin may require levels of 15 to 20% by weight. It has been found that when the amount of titanium dioxide in the sunscreen composition exceeds about 5% by weight the composition may exhibit a blue-white pearl effect which is aesthetically unattractive and limits the amount of titanium dioxide which can be incorporated into a sunscreen composition which is acceptable to the user.

It has been found that particularly beneficial sunscreen compositions have recently become available in which the mean primary particle size of the titanium dioxide particles lies in the range 1 to 100 nm, preferably in the range 5 to 50 nm and more preferably in the range 15 to 30 nm. Titanium dioxide of the above mean primary particle size is usually referred to as "microfine". Suitable grades of titanium dioxide are available from Degussa under the trade designation P25, from Tayca Corporation under the trade designation MT150W, MT600B or MT500B, and from Kemira under the trade designation UV Titan M210.

The titanium dioxide particles may be uncoated, or coated with agents typically used for coating titanium dioxide, including aluminium oxide, silicone oils, silicone dioxide and organic alcohol and mixture thereof. Preferred titanium dioxide particles are coated with aluminium oxide.

The present invention provides a sunscreen composition comprising 0.02 to 30% by weight of titanium dioxide particles, having a mean primary particle size of less than 100 nm and having a dye lake precipitated onto their surface in a dye lake:titanium dioxide ratio of between 10:90 and 80:20. Preferably the ratio is between 20:80 and 70:30.

Preferably the composition comprises 0.5 to 20%, more preferably 1 to 15% by weight of the coated titanium dioxide particles.

A further aspect of the present invention provides a sunscreen composition comprising a water-in-oil emulsion which comprises:

a) 0.02 to 30% by weight of titanium dioxide particles having a mean primary size of less than 100 nm and having a dye precipitated onto their surface in a dye lake:titanium dioxide ratio of between 10:90 and 80:20, b) 5 to 70% by weight of an oil phase, c) 1 to 15% by weight of an emulsifier, and d) at least 20% by weight of an aqueous phase.

A still further aspect of the invention provides a sunscreen composition comprising an oil-in-water emulsion which comprises:

a) 0.02 to 30% by weight of titanium dioxide particles having a mean particle size of less than 100 nm and having a dye precipitated onto their surface in a dye lake:titanium dioxide ratio of between 10:90 and 80:20, b) 5 to 60% by weight of an oil phase, c) 1 to 20% by weight of an emulsifier, and d) at least 35% by weight of an aqueous phase.

Other sunscreening agents may be incorporated into the sunscreen compositions of the present invention. Examples of suitable further sunscreening agents include a) p-aminobenzoic acids, esters and derivatives (for example, 2-ethylhexyl p-dimethylaminobenzoate, or the octyl ester of p-aminobenzoic acid), b) methoxycinnamate esters [for example, 2-ethylhexyl p-methoxycinnamate, 2-ethoxyethyl p-methoxy-cinnamate or $\alpha,\beta$-di-(p-methoxy-cinnamoyl)-$\alpha$'-(2-ethylhexanoyl)glycerin], c) benzo-phenones (for example oxybenzone), d) dibenzoylmethanes and e) salicylate esters.

Any additional sunscreening agent is present in an amount from 0.1 to 10% by weight of the composition.

The oil phase of the sunscreen compositions of the present invention, which are water-in-oil or oil-in-water emulsions may comprise:

a) hydrocarbon oils such as paraffin or mineral oils;

b) waxes such as beeswax or paraffin wax;

c) natural oils such as sunflower oil, apricot kernel oil, shea butter or jojoba oil;

d) silicone oils such as dimethicone, cyclomethicone or cetyldimethicone;

e) fatty acid esters such as isopropyl palmitate or isopropyl myristate;

f) fatty alcohols such as cetyl alcohol or stearyl alcohol; or g) mixtures thereof.

In preferred water-in-oil compositions of the present invention, the oil phase comprises 5 to 60% by weight of the composition. In preferred oil-in-water sunscreen compositions of the present invention, the oil phase comprises 10 to 30% by weight of the composition.

The emulsifiers used may be any emulsifiers known in the art for use in water-in-oil or oil-in-water emulsions. It has been found that particularly effective water-in-oil sunscreen compositions can be prepared by using an emulsifier or mixture of emulsifiers selected from:

a) ethoxylated fatty alcohols, for example the emulsifier available commercially under the trade name Brij (ICI);

b) ethoxylated fatty acids and their esters such as ethoxylated stearates, for example the emulsifier available commercially under the trade name Myrj (ICI);

c) sorbitan esters, such as the emulsifier available commercially under the trade name Span (ICI);

d) ethoxylated sorbitan esters, such as the emulsifier available commercially under the trade name Tween (ICI);

e) ethoxylated mono-di- and tri-glycerides, for example the emulsifier available commercially under the trade name Arlatone (ICI);

f) silicon emulsifiers such as silicone polyols, available commercially for example under the trade name Abil WS08;

g) anionic emulsifiers for example cetylstearyl sulphates available under the trade name Dehydag and anionic esters of mono and diglyercides available under the trade name Grindtek;

h) cationic emulsifiers for example dimethyl-distearylammonium chloride available under the trade name Genamin DSAC.

The amount of emulsifier present in the water-in-oil compositions of the present invention is preferably in the range 1 to 15%.

Particularly effective oil-in-water sunscreen compositions can be prepared by using an emulsifier or mixture of emulsifiers selected from known cosmetically acceptable emulsifiers which include:

a) fatty acid soaps such as potassium stearate, b) ethoxylated fatty alcohols, for example the emulsifier available commercially under the trade name Brij (ICI);

c) sorbitan esters, for example the emulsifier available commercially under the trade name Span (ICI);

d) ethoxylated sorbitan esters, for example the emulsifier available commercially under the trade name Tween (ICI);

e) ethoxylated fatty acid esters such as ethoxylated stearates, for example the emulsifier available commercially under the trade name Myrj (ICI);

f) ethoxylated mono-, di-, and tri-glycerides, for example the emulsifier available commercially under the trade name Arlatone (ICI); or g) mixtures thereof.

The amount of emulsifier present in the oil-in-water compositions of the present invention is preferably in the range 1 to 10%.

The sunscreen compositions of the present invention may additionally comprise other components which will be well known to those skilled in the art for example emollients such as isopropyl myristate or a triglyceride of a fatty acid (e.g. lauric triglyceride or capric/ caprylic triglyceride), moisturisers such as D-panthenol, humectants such as glycerin or 1,3-butylene-glycol, antioxidants such as DL-A-tocopheryl-acetate or butylated hydroxytoluene, emulsion stabilising salts such as sodium chloride, sodium citrate or magnesium sulphate, film formers to assist spreading on the surface of the skin such as alkylated polyvinyl-pyrrolidone, preservatives such as bronopol, sodium dehydroacetate, polyhexamethylenebiguanide hydrochloride, isothiazolone or diazolidinylurea, perfumes and colouring.

It will be appreciated that the present invention includes sunscreen compositions comprising coloured titanium dioxide particles, coloured zinc oxide particles, and mixtures thereof. Compositions containing mixtures of titainium dioxide and zinc oxide particles which have not been coloured as described herein are described in British Patent Specification 2,184,356 and European Patent Applicaiton 433086.

The sunscreen compositions of the present invention described hereinbefore provide adequate protection against both UVA and UVB radiation in a composition which is aesthetically pleasing to the user, thus overcoming the problem of a blue-white tint left on the skin after application of sunscreens containing titanium dioxide which has not been coloured in this way. Preferred sunscreen compositions are substantially transparent when applied to the skin.

A further aspect of the present invention is the use of the coated titanium dioxide particles and/or the coated zinc oxide particles described hereinbefore in cosmetic applications such as face powders, blush powders, eyeshadow powders, lipsticks, mascara, nail polish and foundation creams. The advantage conferred by colouring such products with the said coated particles is to impart protection from the sun's rays or other UV sources when the products are applied to the body, without detracting from the aesthetic effect of the cosmetics. A further advantage conferred by colouring such products with the said coated particles is an improved skin feel, gloss or colour appearance, depending on the level of incorporation.

Each cosmetic and toiletry composition may additionally comprise any other cosmetically approved colourant.

Other sunscreening agents may be incorporated into each cosmetic and toiletry composition of the present invention. Examples of suitable further sunscreening agents include:

a) p-aminobenzoic acids, esters and derivatives (for example, 2-ethylhexyl p-dimethylaminobenzoate, or the octyl ester of p-aminobenzoic acid), b) methoxycinnamate esters (for example, 2-ethylhexyl p-methoxycinnamate, 2-ethoxyethyl p-methoxycinnamate or α, β-di-(p-methoxy-cinnamoyl)-α'-(2ethylhexanoyl)glycerin), c) benzo-phenones (for example, oxybenzone), d) dibenzoylmethanes, and e) salicylate esters Any additional sunscreening agent is present in an amount from 0.1 to 10% by weight of the composition.

A further aspect of the present invention provides a cosmetic or toiletry composition comprising 0.05 to 25% by weight of the coated particles of the present invention together with a cosmetically acceptable diluent or carrier.

The cosmetic or toiletry composition may be:

a) a face powder composition comprising 0.1 to 15.0% by weight of the metal oxide particles, b) a blush powder composition comprising 0.05 to 15% by weight of the metal oxide particles, c) an eye-shadow powder composition comprising 0.5 to 15% by weight of the metal oxide particles, d) a pearly lipstick composition comprising 0.5 to 6% by weight of the metal oxide particles, e) a non-pearly lipstick composition comprising 2 to 8% by weight of the metal oxide particles, f) a mascara composition comprising 0.5 to 15% by weight of the metal oxide particles, g) a nail polish base composition comprising 0.2 to 5% by weight of the metal oxide particles, or h) a foundation cream composition comprising 0.5 to 25% by weight of the metal oxide particles.

The metal oxide particles in the above compositions may be:

a) titanium dioxide particles having a mean primary particle size of less than 100 nm, b) zinc oxide particles having a mean primary particle size of less than 500 nm, or c) mixtures thereof in a ratio of between 1:99 and 90:10 of titanium dioxide:zinc oxide, more preferably of between 5:95 and 60:40.

The compositions of the present invention may additionally comprise other components which will be well known to those skilled in the art.

The invention will now be illustrated by the following non-limiting Examples, which are given by way of example only.

EXAMPLES 1 AND 2

| | |
|---|---|
| 1. Metal Oxide | 70 g |
| 2. FD & C Blue No 1 | 10 g |
| 3. Aluminium chloride hydrate | 15 g |
| 4. Sodium bicarbonate | 6 g |
| 5. Water | 400 g |

Component 1 is slurried into water (300 g) at 10° C. The sodium bicarbonate is added and dissolved. 7 g of the aluminium chloride hydrate dissolved in water (28 g) is very slowly added to this mixture with slow stirring allowing the carbon dioxide gas generated to escape, until the pH reaches 5.5. The dye is then dissolved in water (50 g) and added to the mixture at 20° C. The remaining aluminium chloride dissolved in the remaining water, is added and the mixture is stirred for 2 hours. The resulting slurry is filtered and washed. The resulting pigment is then dried and ground to form particles of a suitable size.

| EXAMPLE | METAL OXIDE |
|---|---|
| 1 | Microfine Titanium Dioxide (sold under the trade name UV-TITAN M210) |
| 2 | Microfine Zinc Oxide (sold by Sunsmart Inc, USA under the trade name Z-COTE) |

| Method A | |
|---|---|
| 1. Metal Oxide | 100.0 g |
| 2. Aluminium chloride hydrate | 10.0 g |
| 3. Sodium bicarbonate | 7.5 g |
| 4. Dye | 2.5 g |
| 5. Water | 465.0 g |

Component 1 is formed into an aqueous slurry (400 g) at 10° C. Component 3 is added and dissolved. Component 2 is dissolved in water (20 g) and added slowly with stirring until the mixture reaches pH 5.5. Stirring is continued for 30 minutes. Component 4 is dissolved in water (45 g) and added. The remaining aluminium chloride solution is added slowly until the pH reaches 4.2. Stirring is continued until all the lake has precipitated onto the metal oxide. The resulting pigment was separated by filtration, then washed, dried and ground to form particles of a suitable size.

The following examples utilize Method A:

EXAMPLES 3–10

| EXAMPLE | METAL OXIDE | DYE |
|---|---|---|
| 3 | Microfine Titanium Dioxide (sold under the trade name UV-TITAN M210) | FD & C Yellow No 5 |
| 4 | Microfine Titanium Dioxide (sold under the trade name UV-TITAN M210) | Acid Yellow 23/ Acid Red 27 mixture (available from FD Anstead Ltd under the trade designation Brown 13693) |
| 5 | Microfine Titanium Dioxide (sold under the trade name UV-TITAN M210) | FD & C Blue No 1 (12.5 g) FD & C Yellow No 8 (1.26 g) |
| 6 | Microfine Titanium Dioxide (sold under the trade name UV-TITAN M210) | Any combination (total 2.5 g) |
| 7 | Microfine Zinc Oxide (sold by Sunsmart Inc., USA under the trade name Z cote) | FD & C Yellow No 5 |
| 8 | Microfine Zinc Oxide (sold by Sunsmart Inc., USA under the trade name Z cote) | Acid Yellow 23/ Acid Red 27 mixture (available from FD Anstead Ltd under the trade designation Brown 13693) |
| 9 | Microfine Zinc Oxide (sold by Sunsmart Inc., USA under the trade name Z cote) | FD & C Blue No 1 (1.25 g) FD & C Yellow No 8 (1.25 g) |
| 10 | Microfine Zinc Oxide (sold by Sunsmart Inc., USA under the trade name Z cote) | Any combination (total 2.5 g) |

| Method B | |
|---|---|
| 1. Metal Oxide | 20 g |
| 2. Alum Solution (5%) | 100 ml |
| 3. Soda Solution (20%) | 25 ml |
| 4. Dye Solution (20%) | 1 ml |
| 5. Aluminium Chloride Solution (25%) | 2 ml |

Component 1 is formed into a slurry with component 2. Component 3 is added slowly until pH 7 is reached. The slurry is thoroughly washed with water, and components 4, then 5 are added. The mixture is stirred until precipitation of the lake onto the metal oxide is complete. The pigment is collected by filtration, washed, dried and ground to form particles of suitable size.

The following examples utilise Method B:

EXAMPLES 11–14

| EXAMPLE | METAL OXIDE | DYE |
|---|---|---|
| 11 | Microfine Titanium Dioxide (sold under the trade name MT150W) | FD & C Blue No 1 |
| 12 | Microfine Titanium Dioxide (sold under the trade name MT150W) | FD & C Blue No 1 (0.5 ml) FD & C Yellow No 5 (0.5 ml) |
| 13 | Microfine Zinc Oxide (available from Sumitomo Cement Co., Japan) | FD & C Blue No 1 |
| 14 | Microfine Zinc Oxide (available from Sumitomo Cement Co., Japan) | FD & C Blue No 1 (0.5 ml) FD & C Yellow No 5 (0.5 ml) |

EXAMPLE 15

| | | |
|---|---|---|
| 1. | Microfine Titanium Dioxide (sold under trade name UV-TITAN M210) | 70.0 g |
| 2. | FD & C Blue No 1 | 5.0 g |
| 3. | Aluminium chloride | 3.4 g |
| 4. | Water | 345.0 g |

Component 1 is formed into an aqueous slurry (300 g). A solution of component 2 in water (25 g) is added. A solution of component 3 in water (20 g) is slowly added until a pH of 4 is reached. The mixture is stirred for a further 2 hours. The resulting pigment is collected by filtration, washed, dried and ground to form particles of a suitable size.

EXAMPLE 16

| | | % w/w |
|---|---|---|
| 1. | Microfine Titanium Dioxide (sold under the trade name UV-TITAN M210 | 70 |
| 2. | Water soluble dye or combination of water soluble dyes | 10 |
| 3. | Soluble salt of calcium, barium, stronium, manganese, aluminium, zinc, copper, iron, titanium, gallium or magnesium | 20 |

Component 1 is formed into an aqueous slurry. Component 3 is dissolved in water and added to the slurry, then component 2 is dissolved in water and added, stirring for 2 hours at a temperature between 10° C. and 95° C. The mixture is filtered, washed and dried. The resulting pigment is ground to form particles of a suitable size.

EXAMPLE 17

|   | | % w/w |
|---|---|---|
| 1. | Microfine Zinc Oxide | 70 |
| 2. | Water soluble dye or combination of water soluble dyes | 10 |
| 3. | Soluble salt of calcium, barium, strontium, manganese, aluminium, zinc, copper, iron, titanium, gallium or magnesium | 20 |

Component 1 is formed into an aqueous slurry. Component 3 is dissolved in water and added to the slurry, then component 2 is dissolved in water and added, stirring for 2 hours at a temperature between 10° C. and 95° C. The mixture is filtered, washed and dried. The resulting pigment is ground to form particles of a suitable size.

EXAMPLE 18

An example of a sunscreen product containing microfine titanium dioxide particles having a dye lake precipitated onto their surface in a dye lake:titanium dioxide ratio of between 10:90 and 80:20 is given below:

|   | | % w/w |
|---|---|---|
| 1. | Hydroxyethylcellulose (sold under the trade name Natrosol 250HHR) | 0.5 |
| 2. | Ethylenediaminetetraacetic acid tetra-sodium salt (sold under the trade name Sequestrene Na4) | 0.1 |
| 3. | 1,3 Butylene Glycol | 5.0 |
| 4. | Coated Microfine Titanium Dioxide powder formed in a similar manner to that described in Method A with a combination of dyes giving a tan colour | 5.0 |
| 5. | Cetearyl alcohol (and) peg.23 stearate sold under the trade name Polawax) | 2.5 |
| 6. | Glyceryl Monostearate (sold under the trade name Monostearin NSE) | 2.0 |
| 7. | Triglyceride of saturated C10–C18 fatty acids (sold under the trade name Softisan 100) | 1.0 |
| 8. | White Soft Paraffin BP | 3.0 |
| 9. | Light Liquid Paraffin WOM14 | 3.0 |
| 10. | Cetyl Alcohol | 1.0 |
| 11. | Water | to 100 |

The emulsion is prepared by dissolving components 2 and 3 in the water and dispersing into this components 1 and 4 whilst at 70° C. Components 5–10 are then heated together to 70°–75° C., added to the water phase using a high shear mixer/homogeniser (Silverson). After 5–10 minutes the product is stir cooled. The result is a tan coloured cream which leaves no white colour on the skin after application.

EXAMPLE 19

A sunscreen composition comprising the following constituents may be prepared:

|   | | % w/w |
|---|---|---|
| 1. | Hydroxyethylcellulose (sold under the trade name Natrosol 250HHR) | 0.5 |
| 2. | Ethylenediaminetetraacetic acid tetra-sodium salt (sold under the trade name Sequestrene Na4) | 0.2 |
| 3. | Ethoxylated Methyl Glucoside Sesqui-stearate sold under the trade name Glucamate (SSE 20) | 2.0 |
| 4. | Methyl Glucoside Sesquistearate (sold under the trade name Glucate SS) | 1.2 |
| 5. | White Soft Paraffin BP | 5.0 |
| 6. | Light Liquid Paraffin WOM14 | 3.0 |
| 7. | Cetyl Alcohol | 3.0 |
| 8. | Pentaerythrityl Tetraisostearate (sold under the trade name Crodamol PTIS) | 2.0 |
| 9. | Ethylene Glycol Esters of fatty wax acids C18–36 (sold under the trade name Syncrowax ERLC) | 2.0 |
| 10. | Combination of coated Microfine Titanium Dioxide powders formed in a similar manner to that described in Method A using different individual dyes which together give a tan coliur | 10.0 |
| 11. | 1,3-Butylene Glycol | 5.0 |
| 12. | Water | to 100 |

Components 2 and 11 are dissolved in the water and heated to 70° C. Components 1 and 10 are then dispersed into the water phase using a high shear mixer/homogeniser (Silverson). The remaining raw materials are heated together to 70°–75° C. and then added to the water phase with further high shear mixing. After 5–10 minutes the emulsion is stir cooled. The resultant cream is tan coloured and after application would leave a degree of whiteness less than would be expected for a product containing 10% of this grade titanium dioxide.

EXAMPLE 20

A sunscreen composition comprising the following constituents may be prepared:

|   | | % w/w |
|---|---|---|
| 1. | Hydroxyethylcellulose (sold under the trade name Natrosol 250HHR) | 5.0 |
| 2. | Ethylenediaminetetraacetic acid tetra-sodium salt (sold under the trade name Sequestrene Na4) | 0.2 |
| 3. | Ethoxylated Methyl Glucoside Sesqui-stearate sold under the trade name Glucamate (SSE 20) | 2.0 |
| 4. | Methyl Glucoside Sequistearate (sold under the trade name Glucate SS) | 1.2 |
| 5. | White Soft Paraffin BP | 5.0 |
| 6. | Light Liquid Paraffin WOM14 | 3.0 |
| 7. | Cetyl Alcohol | 3.0 |
| 8. | Pentaerythrityl Tetraisostearate (sold under the trade name Crodamol PTIS) | 2.0 |
| 9. | Ethylene Glycol Esters of fatty wax acids C18–36 (sold under the trade name Syncrowax ERLC) | 2.0 |
| 10. | Coated Microfine Titanium Dioxide powder that formed in a similar manner to that described in Method A with a combination of dyes giving a tan colour | 5.0 |
| 11. | Coated Microfine Zinc Oxide powder formed in a similar manner to that described in Method A with a combination of dyes giving a tan colour | 5.0 |
| 12. | 1,3-Butylene Glycol | 5.0 |
| 13. | Water | to 100 |

Components 2 and 12 are dissolved in the water and heated to 70° C. Components 1, 10 and 11 are then dispersed into the water phase using a high shear mixer/homogeniser (Silverson). The remaining raw materials are heated together to 70°–75° C. and then added to the water phase with further high shear mixing. After 5–10 minutes, the emulsion is stir cooled. The resultant cream is tan coloured and after application would leave a degree of whiteness less than would be expected for a product containing 5% of this grade of titanium dioxide and 5% of this grade of zinc oxide.

EXAMPLE 21

A face powder composition comprising the following constituents may be prepared:

| | | % w/w |
|---|---|---|
| 1. | Magnesium or Calcium Stearate | 3–8 |
| 2. | Dimethicone and/or Paraffin | 1–6 |
| 3. | Coated Microfine Titanium Dioxide powder formed in a similar manner to that described in Method A | 0.1–15.0 |
| 4. | Talc | to 100 |

EXAMPLE 22

A face powder composition comprising the following constituents may be prepared:

| | | % w/w |
|---|---|---|
| 1. | Magnesium or Calcium Stearate | 3–8 |
| 2. | Dimethicone and/or Paraffin | 1–6 |
| 3. | Coated Microfine Zinc Oxide powder formed in a similar manner to that described in Method A | 0.1–15.0 |
| 4. | Talc | to 100 |

EXAMPLE 23

A blush powder composition comprising the following constituents may be prepared:

| | | % w/w |
|---|---|---|
| 1. | Magnesium or Calcium Stearate | 3–8 |
| 2. | Titanium Dioxide Coated Mica | 5–25 |
| 3. | Dimethicone and/or Paraffin and/or Isopropyl Palmitate | 5–8 |
| 4. | Coated Microfine Titanium Dioxide powder formed in a similar manner to that described in Method A | 0.5–15 |
| 5. | Talc | to 100 |

EXAMPLE 24

A blush powder composition comprising the following constituents may be prepared:

| | | % w/w |
|---|---|---|
| 1. | Magnesium or Calcium Stearate | 3–8 |
| 2. | Titanium Dioxide Coated Mica | 5–25 |
| 3. | Dimethicone and/or Paraffin and/or Isopropyl Palmitate | 5–8 |
| 4. | Coated Microfine Titanium Dioxide powder formed in a similar manner to that described in Method A | 0.25–7.5 |
| 5. | Coated Microfine Zinc Oxide powder formed in a similar manner to that described in Method A | 0.25–7.5 |
| 6. | Talc | to 100 |

EXAMPLE 25

An eyeshadow powder composition comprising the following constituents may be prepared:

| | | % w/w |
|---|---|---|
| 1. | Magnesium or Calcium Stearate | 4–12 |
| 2. | Titanium Dioxide Coated Mica | 5–60 |
| 3. | Dimethicone and/or Paraffin and/or Isopropyl Palmitate | 5–20 |
| 4. | Coated Microfine Titanium Dioxide powder formed in a similar manner to that described in Method A | 0.5–15 |

EXAMPLE 26

A pearly lipstick composition comprising the following constituents may be prepared:

| | | % w/w |
|---|---|---|
| 1. | Carnauba Wax | 1.5 |
| 2. | Beeswax | 8 |
| 3. | Ozokerite | 7 |
| 4. | Condensate of lanolin fatty acids with ethylene oxide (sold under the trade name Lanpol 5 Croda) | 8 |
| 5. | Triglycerides of capric and caprylic acids (sold under the trade name Miglyol 812) | 2 |
| 6. | Castor Oil | 50 |
| 7. | Propylene Glycol | 1.5 |
| 8. | Coated Microfine Titanium Dioxide powder formed in a similar manner to that described in Method A | 0.5–6 |
| 9. | Pearl | 7–20 |
| 10. | Mixture of fatty alcohols, chiefly oleyl alcohol (sold under the trade name Novol Croda) | 18 |

EXAMPLE 27

A non-pearly lipstick composition comprising the following constituents may be prepared:

| | | % w/w |
|---|---|---|
| 1. | Carnauba Wax | 4 |
| 2. | Beeswax | 4 |
| 3. | Ozokerite | 4 |
| 4. | Cetyl Alcohol | 0.6 |
| 5. | A standard blend of ozokerite (sold under the trade name Okerin Wax 239) | 0.8 |
| 6. | Condensate of lanolin fatty acids with ethylene oxide (sold under the trade name Lanpol 5 Croda) | 10 |

-continued

|   |   | % w/w |
|---|---|---|
| 7. | Mixture of fatty alcohols, chiefly oleyl alcohol (sold under the trade name Novol Croda) | 23 |
| 8. | Castor Oil | 50 |
| 9. | Coated Microfine Titanium Dioxide powder formed in a similar manner to that described in Method A | 5 |

EXAMPLE 28

A mascara composition comprising the following constituents may be prepared:

|   |   | % w/w |
|---|---|---|
| 1. | Carnauba Wax | 8 |
| 2. | Beeswax | 8 |
| 3. | A standard blend of Ozokerite (sold under the trade name Okerin Wax) | 8 |
| 4. | Stearic Acid | 6.3 |
| 5. | C11–C13 Isoparaffin (sold under the trade name Isopar) | 5.0 |
| 6. | Triethanolamine | 5.0 |
| 7. | Coated Microfine Titanium Dioxide powder formed in a similar manner to that described in Method A | 0.5–15 |
| 8. | Synthetic Magnesium Aluminum Silicate (sold under the trade name Veegum) | 2.4 |
| 9. | Lecithin | 0.45 |
| 10. | 1,3-Butylene Glycol | 3 |
| 11. | Film former comprising ammonium acrylates copolymer, propylene glycol and potassium octoxynol-12 phosphate and non-oxynol-10 (sold under the trade name Syntran 5170) | 10 |
| 12. | Water | to 100% |

EXAMPLE 29

A nail polish base composition comprising the following constituents may be prepared:

|   |   | % w/w |
|---|---|---|
| 1. | Nitrocellulose | 10 |
| 2. | Resin | 10 |
| 3. | Plasticiser | 5 |
| 4. | Alcohol | 5 |
| 5. | Ethyl Acetate | 20 |
| 6. | Butyl Acetate | 15 |
| 7. | Toluene | 35 |
| 8. | Coated Microfine Titanium Dioxide powder formed in a similar manner to that described in Method A | 0.2–5% |

EXAMPLE 30

A foundation cream composition comprising the following constituents may be prepared:

|   |   | % w/w |
|---|---|---|
| 1. | Glycerin | 5 |
| 2. | Xanthan Gum | 0.2 |
| 3. | Cetearyl alcohol (and) PEG 23 stearate (sold under the trade name Polawax) | 2.5 |
| 4. | Stearic Acid Toilet | 0.5 |
| 5. | Petrolatum | 1.0 |
| 6. | Cetyl Alcohol | 0.7 |
| 7. | Dimethicone | 4.5 |
| 8. | Arachidyl Propionate | 2.5 |
| 9. | Cocoa Butter | 1.5 |
| 10. | Cetearyl Octanoate | 1.5 |
| 11. | Mineral Oil | 5 |
| 12. | Potassium Hydroxide | 0.07 |
| 13. | Powdered Nylon | 1 |
| 14. | Colour Paste (comprising coated Microfine Titanium Dioxide powder, formed in a similar manner to that described in Method A, 50%, in 1,3-butylene glycol, 50%) | 0.5–25 |
| 15. | Water | to 100% |

EXAMPLE 31

A foundation cream composition comprising the following constituents may be prepared:

|   |   | % w/w |
|---|---|---|
| 1. | Glycerin | 5 |
| 2. | Xanthan Gum | 0.2 |
| 3. | Cetearyl alcohol (and) PEG 23 stearate (sold under the trade name Polawax | 2.5 |
| 4. | Stearic Acid Toilet | 0.5 |
| 5. | Petrolatum | 1.0 |
| 6. | Cetyl Alcohol | 0.7 |
| 7. | Dimethicone | 4.5 |
| 8. | Arachidyl Propionate | 2.5 |
| 9. | Cocoa Butter | 1.5 |
| 10. | Cetearyl Octanoate | 1.5 |
| 11. | Mineral Oil | 5 |
| 12. | Potassium Hydroxide | 0.07 |
| 13. | Powdered Nylon | 1 |
| 14. | Colour Paste (comprising coated Microfine Zinc Oxide powder, formed in a similar manner to that described in Method A, 50%, in 1,3-butylene glycol, 50%) | 0.5–25 |
| 15. | Water | to 100% |

We claim:

1. A sunscreen composition comprising 0.02 to 30% by weight of titanium dioxide particles having a mean primary particle size of less than 100 nm and having a dye Lake precipitated onto their surface in a dye lake:titanium dioxide ratio of between 10:90 and 80:20.

2. A sunscreen composition comprising 0.02 to 30% by weight of zinc oxide particles having a mean primary particle size of less than 500 nm and having a dye lake precipitated onto their surface in a dye lake:zinc oxide ratio of between 10:90 and 80:20.

3. A sunscreen composition as claimed in claim 1 comprising a water-in-oil emulsion which comprises:
   a) 0.02 to 30% by weight of titanium dioxide particles having a mean primary size of less than 100 nm and having a dye lake precipitated onto their surface in a dye lake:titanium dioxide ratio of between 10:90 and 80:20,
   b) 5 to 70% by weight of an oil phase, c) 1 to 15% by weight of an emulsifier, and d) at least 20% by weight of an aqueous phase.

4. A sunscreen composition as claimed in claim 1 comprising an oil-in-water emulsion which comprises: a) 0.02 to 30% by weight of titanium dioxide particles having a mean primary particle size of less than 100 nm and having a dye lake precipitated onto their surface in a dye lake:titanium dioxide ratio of between 10:90 and 80:20, b) 5 to 60% by weight of an oil phase, c) 1 to 20% by weight of an emulsifier, and d) at least 35% by weight of an aqueous phase.

5. A sunscreen composition as claimed in claim 1 additionally containing zinc oxide particles having a mean primate particle size of less than 500 nm and having a dye lake precipitated onto their surface in a dye lake:zinc oxide ratio of between 10:90 and 80:20.

6. A sunscreen composition as claimed in claim 3, additionally containing zinc oxide particles having a mean primary particle size of less than 500 nm and having a dye lake precipitated onto their surface in a dye lake:zinc oxide ratio of between 10:90 and 80:20.

7. A sunscreen composition as claimed in claim 4, additionally containing zinc oxide particles having a mean primary particle size of less than 500 nm and having a dye lake precipitated onto their surface in a dye lake:zinc oxide ratio of between 10:90 and 80:20.

* * * * *